US012667708B2

(12) United States Patent
Underwood et al.

(10) Patent No.: US 12,667,708 B2
(45) Date of Patent: Jun. 30, 2026

(54) PROTECTIVE MEMBRANE FOR MEDICAL LUER CONNECTORS

(71) Applicant: CareFusion 303, Inc., San Diego, CA (US)

(72) Inventors: Wesley Underwood, Placentia, CA (US); Jason Andrew Wine, Placentia, CA (US)

(73) Assignee: CAREFUSION 303, INC., San Diego, CA (US)

( * ) Notice: Subject to any disclaimer, the term of this patent is extended or adjusted under 35 U.S.C. 154(b) by 946 days.

(21) Appl. No.: 17/224,975

(22) Filed: Apr. 7, 2021

(65) Prior Publication Data

US 2022/0323740 A1     Oct. 13, 2022

(51) Int. Cl.
 *A61M 39/16*     (2006.01)
 *A61L 2/206*     (2026.01)
 *A61L 103/15*     (2026.01)
 *A61M 39/14*     (2006.01)

(52) U.S. Cl.
 CPC ............. *A61M 39/16* (2013.01); *A61L 2/206* (2013.01); *A61M 39/14* (2013.01); *A61L 2103/15* (2026.01); *A61M 2205/7527* (2013.01)

(58) Field of Classification Search
 CPC .................. A61M 39/16; A61M 39/14; A61M 2205/7527; A61M 2005/3104; A61L 2/206; A61L 2202/24
 See application file for complete search history.

(56) References Cited

U.S. PATENT DOCUMENTS

| | | | |
|---|---|---|---|
| 5,125,415 A * | 6/1992 | Bell .................. | A61B 5/150213 604/199 |
| 5,451,374 A | 9/1995 | Molina | |
| 5,615,772 A * | 4/1997 | Naganuma ............ | A61M 5/002 604/220 |
| 5,807,343 A | 9/1998 | Tucker et al. | |
| 2006/0253103 A1* | 11/2006 | Utterberg .............. | A61M 39/02 604/533 |
| 2009/0149817 A1* | 6/2009 | Frezza ................ | A61M 5/3134 604/198 |

(Continued)

FOREIGN PATENT DOCUMENTS

| | | | |
|---|---|---|---|
| CA | 2618923 A1 * | 7/2008 | ............ A61M 39/20 |
| EP | 0832658 B1 | 12/2003 | |

(Continued)

OTHER PUBLICATIONS

International Search Report and Written Opinion for Application No. PCT/US2022/022388, dated Jul. 19, 2022, 14 pages.

(Continued)

*Primary Examiner* — Lauren P Farrar

(74) *Attorney, Agent, or Firm* — MASCHOFF BRENNAN

(57) ABSTRACT

A protective membrane for a medical luer connector may include a cover having an upper surface, a lower surface having a mating portion for coupling to a mating surface of the medical luer connector, and an outer perimetal surface. The protective membrane may further include a flexible pull tab extending from the outer perimetal surface of the cover, and an adhesive overlaying the mating portion of the lower surface for adhering to the mating surface of the medical luer connector.

20 Claims, 6 Drawing Sheets

(56)     References Cited

U.S. PATENT DOCUMENTS

| | | | | | |
|---|---|---|---|---|---|
| 2009/0281504 | A1* | 11/2009 | Nanba | ..................... | A61M 5/28 |
| | | | | | 604/222 |
| 2010/0292673 | A1* | 11/2010 | Korogi | ................. | A61M 39/20 |
| | | | | | 604/533 |
| 2012/0220955 | A1* | 8/2012 | Maseda | ................. | A61M 39/20 |
| | | | | | 604/256 |
| 2013/0030414 | A1* | 1/2013 | Gardner | ............... | A61M 39/20 |
| | | | | | 604/533 |
| 2014/0262894 | A1* | 9/2014 | Jansen | ................... | B32B 27/12 |
| | | | | | 206/439 |
| 2014/0358115 | A1 | 12/2014 | Chelak et al. | | |
| 2015/0090625 | A1 | 4/2015 | Bauss | | |
| 2015/0320926 | A1* | 11/2015 | Fitzpatrick | .......... | A61M 1/3666 |
| | | | | | 604/244 |
| 2020/0164161 | A1* | 5/2020 | Murray | ................... | B65B 3/003 |
| 2021/0146114 | A1* | 5/2021 | Grant | ............... | A61M 39/0208 |

FOREIGN PATENT DOCUMENTS

| | | |
|---|---|---|
| JP | H10155904 A | 6/1998 |
| JP | 2012510330 A | 5/2012 |
| JP | 2015066225 A | 4/2015 |

OTHER PUBLICATIONS

European Office Action for Application No. 22718390.2, dated Nov. 7, 2025, 7 pages.
Japanese Office Action for Application No. 2023-561658, dated Dec. 2, 2025, 6 pages including translation.
India Patent Office Action for Application No. 202317065134, dated May 5, 2026, 7 pages.

* cited by examiner

PROTECTIVE MEMBRANE FOR MEDICAL LUER CONNECTORS

TECHNICAL FIELD

The present disclosure relates generally to protective membranes for medical luers, and, in particular, to protective membranes configured to maintain the sterility of the medical luer until the IV set is ready to be primed, while decreasing the force required for removal thereof to prepare the IV set for use.

BACKGROUND

Medical luer connectors as used in medical applications are generally designed to be connected to a patient's IV line, drug or solution source, or other medical implements. For example, in IV dispensing systems, a male luer connector may be connected to a fluid source, and a female needleless luer connector having a needless valve may be connected to a catheter via an infusion line.

It is important to keep an exposed surface of the medical luer connector sterile prior to priming and/or administration of a medical fluid to a patient. Unless such sterility is maintained on the exposed surface, any microbes (e.g., bacteria) that may be present on the exposed surface can find their way into a patient's blood stream via a catheter, thereby exposing the patient to a serious health risk associated with bloodstream infections caused by the microbes.

Typically, a luer connector cap may be used to attempt to maintain sterility of the exposed surface of the medical luer connector. However, it is not uncommon for current luer connector caps to be difficult to remove by the clinician, requiring a substantial amount of force to remove the luer connector cap from the luer connector. Further, removal and re-usage of the protective luer connector cap may lead to potential loss of cap sterility, thereby exposing the exposed surface to bacteria that can find their way into a patient's blood stream via a catheter, as described above.

The description provided in the background section should not be assumed to be prior art merely because it is mentioned in or associated with the background section. The background section may include information that describes one or more aspects of the subject technology.

SUMMARY

In accordance with various embodiments of the present disclosure, a protective membrane for a medical luer connector may include a cover having an upper surface, a lower surface having a mating portion for coupling to a mating surface of the medical luer connector, and an outer perimetal surface. The protective membrane may further include a flexible pull tab extending from the outer perimetal surface of the cover, and an adhesive overlaying the mating portion of the lower surface for adhering to the mating surface of the medical luer connector.

In accordance with various embodiments of the present disclosure, a protective membrane for a medical luer connector may include a cover including an upper surface, a lower surface having a mating portion for coupling to a mating surface of the medical luer connector, and an outer perimetal surface. An adhesive may be disposed on the mating portion of the lower surface for adhering to the mating surface of the medical luer connector. The protective membrane for a medical luer connector may further include a flexible pull tab extending from the outer perimetal surface of the cover, an aperture disposed on the cover extending through the upper and lower surfaces, and a filter disposed in the aperture between the upper and lower surfaces of the cover.

In accordance with various embodiments of the present disclosure, a protective membrane for a medical luer connector may include a thin-filmed sleeve including an exterior surface and an interior surface for coupling to an outer surface of the medical luer connector. The thin-filmed sleeve may be formed of a heat-activatable material which upon exposure to heat is configured to shrink from a first diameter of the interior surface to a second diameter of the interior surface where the interior surface has an interference fit with at least a portion of the outer surface of the medical luer connector and seals a sterile portion of the medical luer connector.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 2:
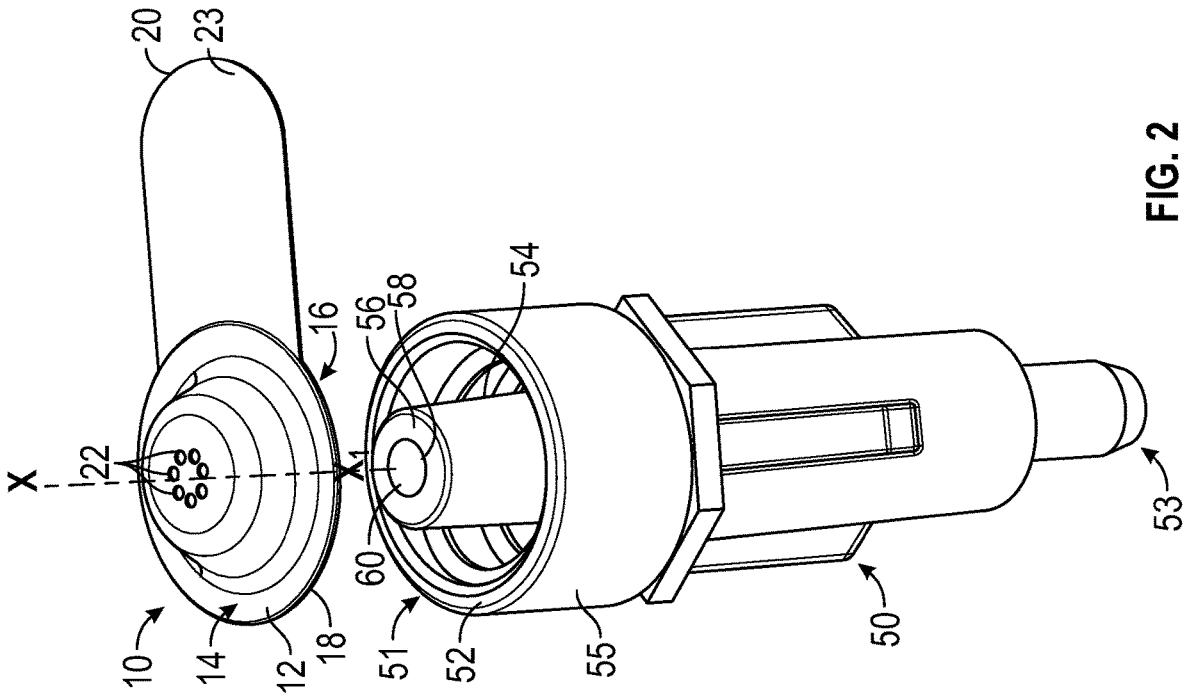
FIG. 2 is a perspective view of the medical luer connector including protective membrane in an uncoupled configuration, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular, but non-limiting, examples. Various embodiments described in the present disclosure may be carried out in different ways and variations, and in accordance with a desired application or implementation.

Various embodiments of the present disclosure are generally directed to protective membranes for medical luers, and, in particular, to protective membranes configured to maintain the sterility of the medical luer until the IV set is ready to be primed, while decreasing the force required for removal thereof to prepare the IV set for use.

As used herein, the terms "medical connector," "connector," "fitting," and any variation thereof refer to any device used to provide a fluid flow path between fluid lines coupled thereto. For example, the medical connector may be or include a bond pocket or other types of connectors. Additionally, the terms "medical connector," "connector," "fitting," and any variation thereof refer to any device used to deliver liquids, solvents, or fluids to or from a patient under medical care. For example, the medical connector may be used for intravenous (IV) delivery of fluids, fluid drainage, oxygen delivery, a combination thereof, and the like to the patient.

In some embodiments, a protective membrane for a medical luer connector may include a cover having an upper surface, a lower surface, and an outer perimetal surface. The outer perimetal surface may be configured as a surface to which a flexible pull tab for removably coupling the protective membrane to the medical luer connector. In some embodiments, the structure for removably coupling the protective membrane to the medical luer connector may be in the form of a flexible pull tab. The flexible pull tab may extend from and/or otherwise form a part of the outer perimetal surface of the cover and may be in the form of a thin flexible flap that may be rotatable, bendable, or otherwise pivotable in order for pull tab to be pulled radially outwards and removed from the medical luer connector.

The lower surface of the protective membrane may include a mating portion which interfaces with and couples to a corresponding mating surface of the medical luer connector. In some embodiments, the medical luer connector may be a male luer connector. However, the various embodiments of the present disclosure are not limited to the aforementioned configuration, and in some embodiments, the medical luer connector may be a female luer connector. The mating portion of the protective membrane may include an adhesive disposed on and/or overlaying the lower surface for adhering to the corresponding mating surface of the medical luer connector. Advantageously, the adhesive may provide a bond and seal between the protective membrane and the medical luer connector having strength and durability that maintains adhesion of the protective membrane to the medical luer connector, but also allows for the protective membrane to be removed, detached or otherwise decoupled from the medical luer connector with relative ease using less force as compared to currently existing luer protector caps conventionally used to maintain sterility of medical luer connectors.

Due to the flexibility of pull tab, the protective membrane may be easily removed and discarded from the medical luer connector prior to priming or other use of the IV set. Advantageously, the protective membrane is not reusable, thereby avoiding the risk of loss of sterility commonly associated with currently existing protective caps for medial luers which may be reused depending on the clinician or other healthcare professional. For example, once the protective membrane is removed from the medical luer connector, the adhesive may no longer exhibit bond strength to maintain adhesion with and seal the medical luer connector, and thus may not be reusable. In contrast, although reuse of current protective luer caps is not recommended due to loss of cap sterility, it is up to the clinician or other healthcare professional to follow guidelines.

In some embodiments, a protective membrane for a medical luer connector may include a thin-filmed sleeve having an exterior surface and an interior surface or coupling to a housing or outer surface of the medical luer connector. The thin-filmed sleeve may be formed of a heat-activatable material which upon exposure to heat is configured to shrink or otherwise reduce in size from a first internal diameter to a second internal diameter. When the thin-filmed sleeve is in the shrunken configuration where the second diameter is smaller than the first unshrunken diameter, the protective membrane may have an interference fit with at least a portion of the housing or outer surface of the medical luer connector.

The aforementioned configuration of the protective membrane formed of a heat-activated material is advantageous in that the shrunken thin-filmed sleeve 17 may tightly seal sterile internal portions of the medical luer connector 50 without adding additional components and weight as a conventional luer protector cap would. Additionally, the configuration of the thin-filmed sleeve 17 is further advantageous in that it allows for the protective membrane 13 to be removed, detached or otherwise decoupled from the medical luer connector 50 with relative ease using less force as compared to currently existing luer protector caps conventionally used to maintain sterility of medical luer connectors.

The protective membranes of the various embodiments described herein thus offer several advantages as compared with conventional or currently existing protective luer caps which require more bulk material to manufacture, thus adding cost, and which often require more force to be used to remove from the medical luer connectors to which they are attached.

Figure 1:
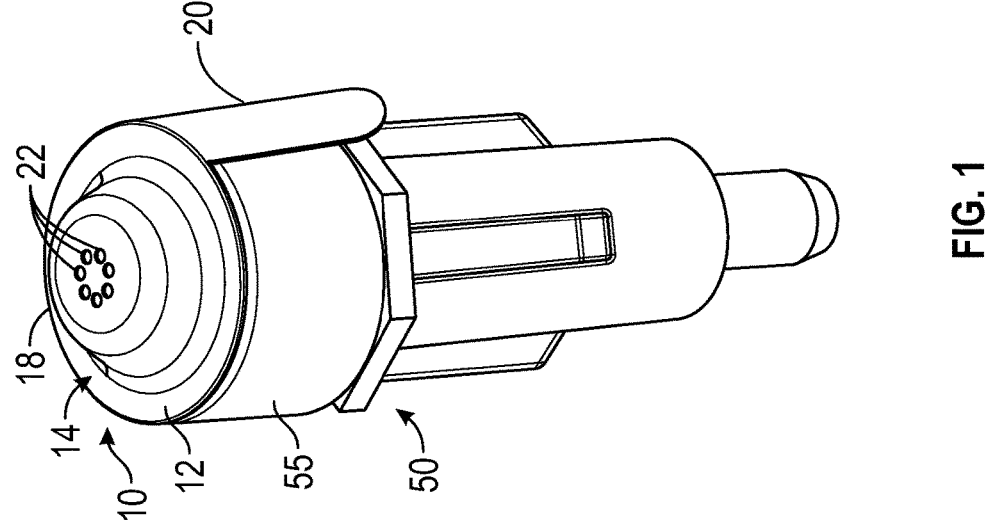
FIG. 1 is a perspective view of a medical luer connector including a protective membrane in a coupled configuration, in accordance with some embodiments of the present disclosure.

FIG. 1 is a perspective view of a medical luer connector including a protective membrane in a coupled configuration, in accordance with some embodiments of the present disclosure. FIG. 2 is a perspective view of the medical luer connector including protective membrane in an uncoupled configuration, in accordance with some embodiments of the present disclosure. According to various embodiments of the present disclosure, a protective membrane 10 for a medical luer connector 50 may include a cover 12 having an upper surface 14, a lower surface 16 (more clearly illustrated in FIG. 4) and an outer perimetal surface 18. The upper surface 14 may be configured as the interface between the cover 12 and an outside and potentially non-sterile environment. The lower surface 16 may be configured as an interface between the cover and a mating surface of the medical luer connector 50. The outer perimetal surface 18 may be configured as a surface to which a structure for removably coupling the protective membrane 10 to the medical luer connector 50. In some embodiments, the structure for removably coupling the protective membrane 10 to the medical luer connector 50 may be in the form of a flexible pull tab 20. The flexible pull tab 20 may include an outer surface 23 and an inner surface 25 for coupling to a housing or outer surface 55 of the medical connector 50, as shall be described in further detail below. However, in some embodiments, the pull tab 20 may not be directly coupled to the outer surface 55, but instead be positioned adjacent to the outer surface 55 without being directly coupled to the outer surface 55, but with a spacing therebetween.

As depicted, the flexible pull tab 20 may extend from and/or otherwise form a part of the outer perimetal surface 18 of the cover 12. In some embodiments, the flexible pull tab 20 may be in the form of a thin flexible flap that may be rotatable, bendable, or otherwise pivotable in order for pull tab 20 to be pulled radially outwards from the position shown in FIG. 1 to at least the position illustrated in FIG. 2. Accordingly, in some embodiments, the pull tab 20 may be rotatable, bendable, or otherwise pivotable about the outer perimetal surface 18 for ease of securing and removing the protective membrane from the medical luer connector. However, the various embodiments of the present disclosure are not limited to the aforementioned configuration. In some embodiments, the pull tab 20 may extend from and/or otherwise form a part of the upper surface 14 and may be rotatable, bendable, or otherwise pivotable in order for pull tab 20 to be pulled radially outwards from the position shown in FIG. 1 to at least the position illustrated in FIG. 2. In yet other embodiments, the pull tab 20 may extend from and/or otherwise form a part of the lower surface 16 and may be rotatable, bendable, or otherwise pivotable in order for pull tab 20 to be pulled radially outwards from the position shown in FIG. 1 to at least the position illustrated in FIG. 2.

Figures 3, 4, 5:
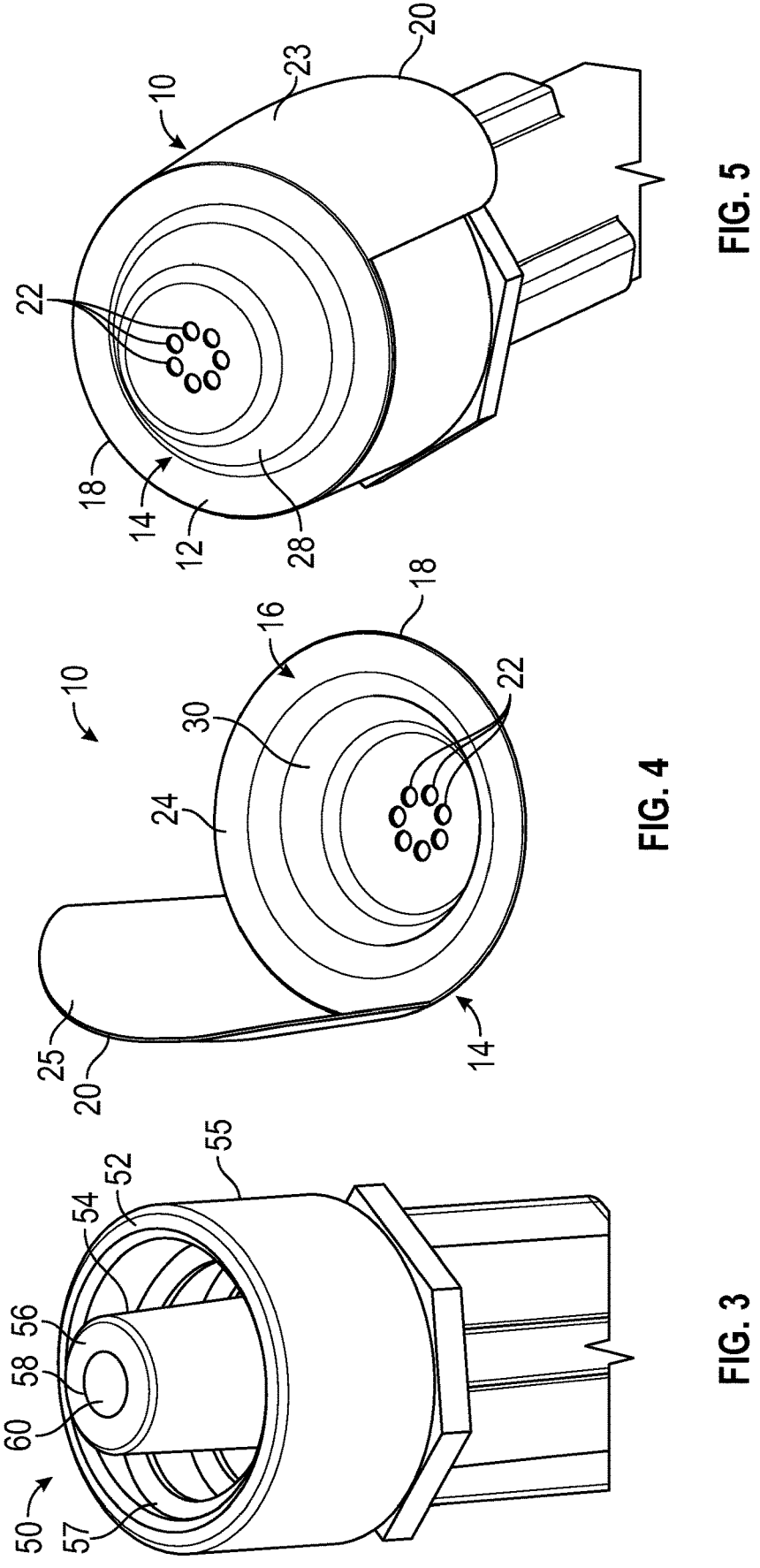
FIG. 3 is a perspective view of the medical luer connector, in accordance with some embodiments of the present disclosure.
FIG. 4 is a bottom perspective view of the protective membrane, in accordance with some embodiments of the present disclosure.
FIG. 5 is a perspective partial view of the medical luer connector including protective membrane in the coupled configuration, in accordance with some embodiments of the present disclosure.

FIG. 3 is a perspective view of the medical luer connector, in accordance with some embodiments of the present disclosure. FIG. 4 is a bottom perspective view of the protective membrane, in accordance with some embodiments of the present disclosure. Referring to FIG. 3, with continued reference to FIGS. 1 and 2, in some embodiments, the medical luer connector 50 may be a male luer. For example, as illustrated in FIG. 3, the housing or outer surface 55 may have a first luer screw thread 57 formed therein. The medical luer connector 50 may further include a male luer portion 54 defining a lumen 60 extending along a central longitudinal axis $X_1$ of the medical luer connector 50. As depicted in FIG. 2, the central longitudinal axis $X_1$ may be coaxially located with the central longitudinal axis X of the cover 12. In some embodiments, the medical connector 50 may be connected at the proximal end 53 to a syringe (not shown), but in other embodiments, the proximal end 53 of medical connector 50 may be connected to a fluid source (e.g., an IV bag) via an IV tubing or other connection. In some embodiments, the distal end of the medical connector 50 including the male luer portion 54 may be connected to an inlet port of a female luer connector in order to fluidly communicate a lumen of the female luer connector to the lumen of the male medical luer connector 50. Further, in some embodiments, the housing or outer surface 55 may define a mating surface 52 at the distal end 51 for mating and adhering with a corresponding mating portion 24 of the lower surface 16, as described below.

In some embodiments, the lower surface 16 of the cover 12 may have a curved or rounded conical profile so as to accommodate the male luer portion 54 therein in the coupled configuration of the protective membrane 10 and the medical luer connector 50. However, the lower surface 16 of the cover 12 of the present disclosure is not limited to the aforementioned configuration. In other embodiments, the lower surface 16 may have a planar profile, for example for coupling with a female luer connector which does not include a male luer portion.

According to various embodiments of the present disclosure, as previously discussed, the lower surface 16 of the protective membrane 10 may be configured as an interface between the cover and a mating surface of the medical luer connector 50. In particular, lower surface 16 of the protective membrane 10 may include a mating portion 24 which interfaces with and couples to a corresponding mating surface 52 of the male medical luer connector 50. The mating portion 24 may include an adhesive disposed on and/or overlaying the mating portion 24 for adhering to the mating surface 52 of the medical luer connector 50. In some embodiments, the adhesive may be an adhesive coating on the mating portion 24 of the lower surface 16. In some embodiments, the adhesive may be an adhesive layer which is removably coupled to the mating portion 24 of the lower surface 16.

Advantageously, the adhesive may provide a bond between the mating portion 24 and the mating surface 52 having strength and durability that maintains adhesion of the protective membrane 10 to the medical luer connector 50, but also allows for the protective membrane 10 to be removed, detached or otherwise decoupled from the medical luer connector 50 with relative ease using less force as compared to currently existing luer protector caps conventionally used to maintain sterility of medical luer connectors.

FIG. 5 is a perspective partial view of the medical luer connector including protective membrane in the coupled configuration, in accordance with some embodiments of the present disclosure. As depicted, in the coupled configuration of the protective membrane 10 and the medical luer connector 50, the mating portion 24 of the lower surface 16 having the adhesive thereon is adhered to the mating surface 52 of the medical luer connector 50. The adhesion of the lower surface 16 to the mating surface 52 creates a seal therebetween to maintain sterility of internal portions or surfaces, for example, surfaces 56 and 58 of the medical luer connector 50. As further depicted in FIG. 5, in the coupled configuration of the protective membrane 10 and the medical luer connector 50, the flexible pull tab 20 extends longitudinally along and is removably coupled to a housing or outer surface 55 of the medical luer connector 50. In particular, in some embodiments, the inner surface 25 of the flexible pull tab 20 may interface with and be coupled to the outer surface or housing 55. Due to the flexibility of pull tab 20, the inner surface 25 may be pulled and peeled away or otherwise decoupled from the housing or outer surface 55. The protective membrane 10 may thus be easily removed and discarded from the medical luer connector prior to priming or other use of the IV set. Advantageously, the protective membrane 10 by design as described above is not reusable, thereby avoiding the risk of loss of sterility commonly associated with currently existing protective caps for medial luers which may be reused depending on the clinician or other healthcare professional. For example, once the protective membrane 10 is removed from the medical luer connector, the adhesive may no longer exhibit bond strength to maintain adhesion with and seal the medical luer connector, and thus may not be reusable. In contrast, although reuse of current protective luer caps is not recommended due to loss of cap sterility, it is up to the clinician or other healthcare professional to follow guidelines.

According to various embodiments of the present disclosure, the protective membrane 10 may further include at least one aperture 22 disposed on the cover 12 and extending through the upper and lower surfaces 14 and 16. In some embodiments a plurality of apertures 22 may be circumferentially disposed about the central longitudinal axis X of the cover 12. In particular, the plurality of apertures 22 may be advantageously positioned over the lumen 60 of the male luer portion 54 to permit ethylene oxide sterilization of the medical luer connector 50.

Figure 7:
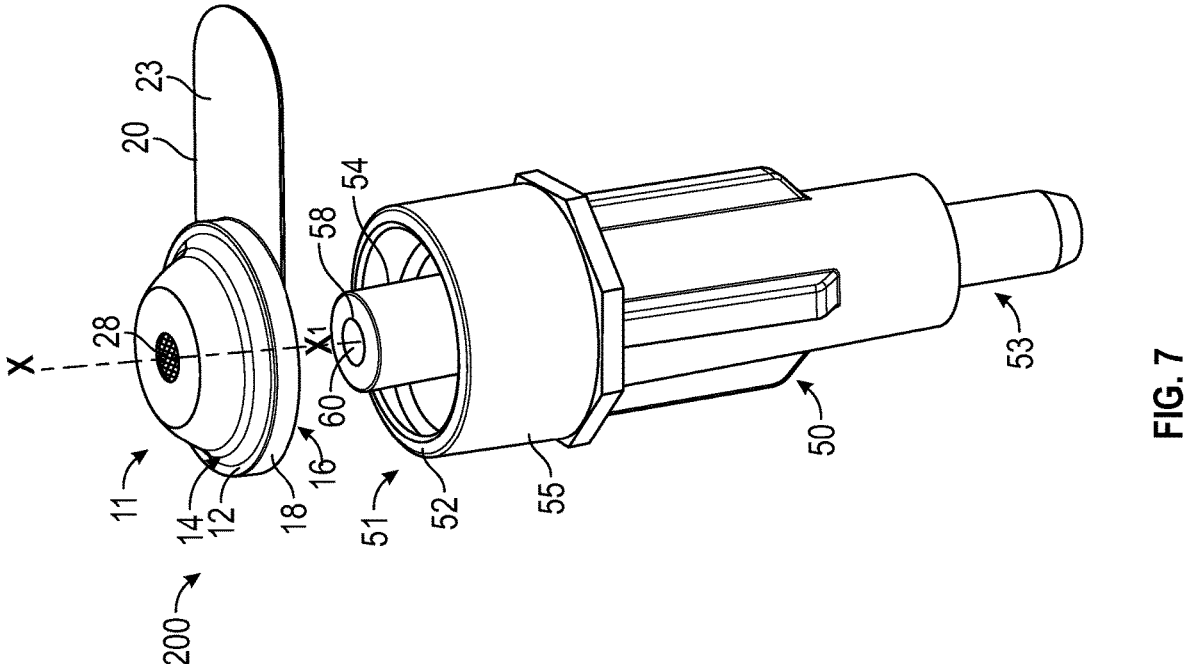
FIG. 7 is a perspective view of the medical luer connector including protective membrane in an uncoupled configuration, in accordance with some embodiments of the present disclosure.
Figure 6:
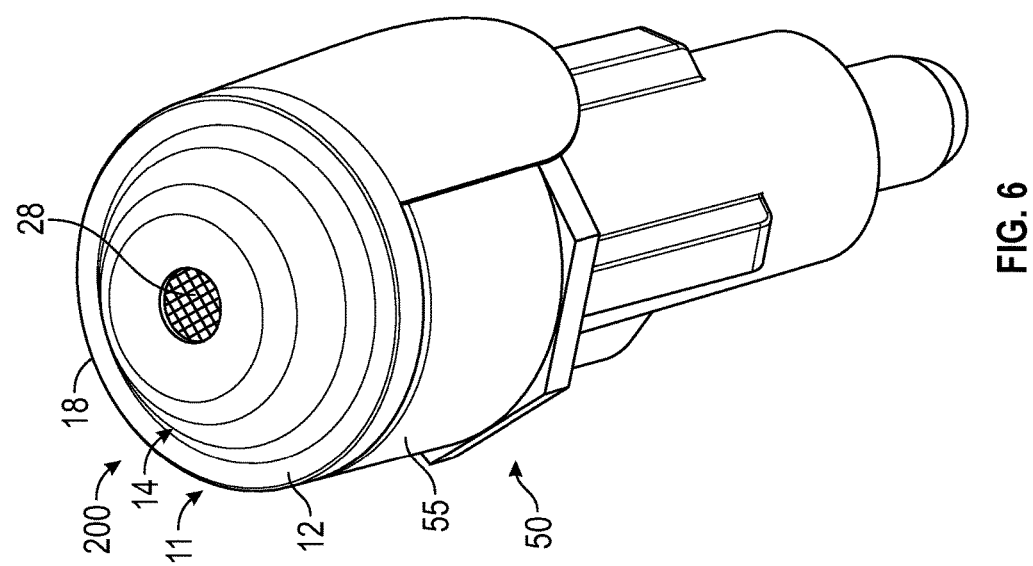
FIG. 6 is a perspective view of a medical luer connector including a protective membrane in a coupled configuration, in accordance with some embodiments of the present disclosure.

FIG. 6 is a perspective view of a medical luer connector 50 including a protective membrane 11 in a coupled configuration, in accordance with some embodiments of the present disclosure. FIG. 7 is a perspective view of the medical luer connector 50 including protective membrane 11 in an uncoupled configuration, in accordance with some embodiments of the present disclosure.

Referring to FIG. 6, similar to the embodiments of FIG. 1, the protective membrane 11 for a medical luer connector 50 may include a cover 12 having an upper surface 14, a lower surface 16 (more clearly illustrated in FIG. 9) and an outer perimetal surface 18. The upper surface 14 may be configured as the interface between the cover 12 and an outside and potentially non-sterile environment. The lower surface 16 may be configured as an interface between the cover 12 and a mating surface of the medical luer connector 50. The outer perimetal surface 18 may be configured as a surface to which a structure for removably coupling the protective membrane 11 to the medical luer connector 50. In some embodiments, the structure for removably coupling the protective membrane 11 to the medical luer connector 50 may be in the form of a flexible pull tab 20. The flexible pull tab 20 may include an outer surface 23 and an inner surface 25 for coupling to a housing or outer surface 55 of the medical connector 50, as shall be described in further detail below.

In accordance with some embodiments, similar to the protective membrane 10, the flexible pull tab 20 of protective membrane 11 may extend from and/or otherwise form a part of the outer perimetal surface 18 of the cover 12. In some embodiments, the flexible pull tab 20 may be in the form of a thin flexible flap that may be rotatable, bendable, or otherwise pivotable in order for pull tab 20 to be pulled radially outwards from the position shown in FIG. 6 to at least the position illustrated in FIG. 7. Accordingly, in some embodiments, the pull tab 20 may be rotatable, bendable, or otherwise pivotable about the outer perimetal surface 18 for ease of securing and removing the protective membrane from the medical luer connector. However, the various embodiments of the present disclosure are not limited to the aforementioned configuration. In some embodiments, the pull tab 20 may extend from and/or otherwise form a part of the upper surface 14 and may be rotatable, bendable, or otherwise pivotable in order for pull tab 20 to be pulled radially outwards from the position shown in FIG. 6 to at least the position illustrated in FIG. 7. In yet other embodiments, the pull tab 20 may extend from and/or otherwise form a part of the lower surface 16 and may be rotatable, bendable, or otherwise pivotable in order for pull tab 20 to be pulled radially outwards from the position shown in FIG. 6 to at least the position illustrated in FIG. 6.

Figure 8:
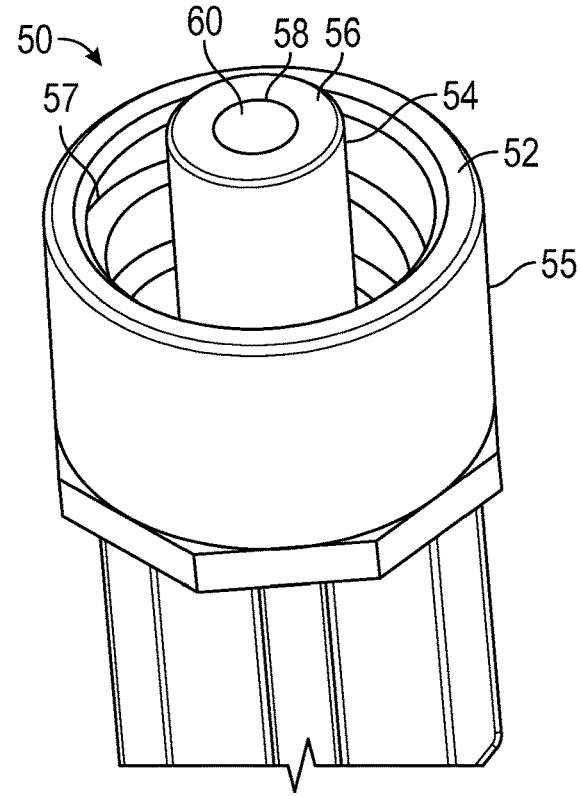
FIG. 8 is a perspective view of the medical luer connector, in accordance with some embodiments of the present disclosure.
Figure 9:
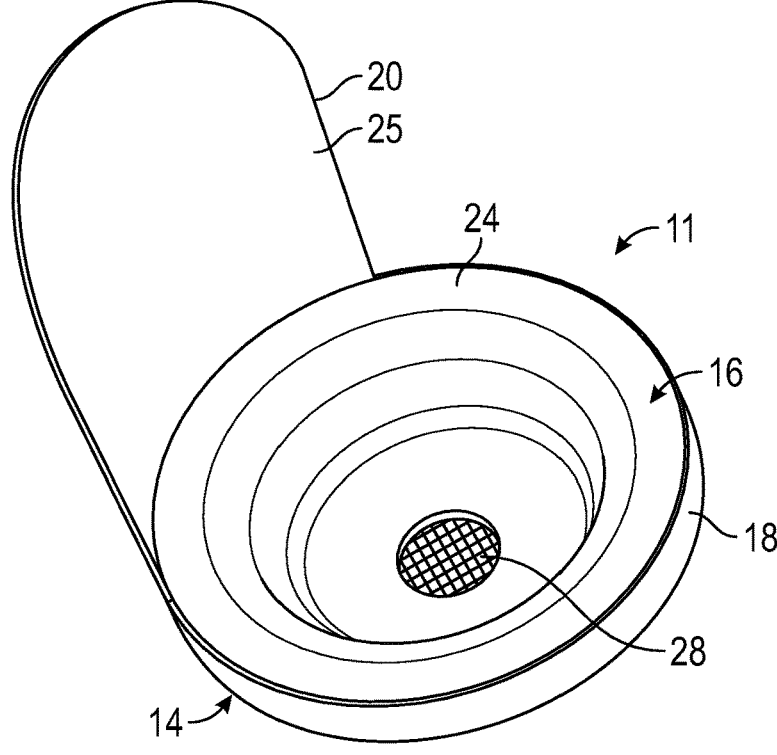
FIG. 9 is a bottom perspective view of the protective membrane, in accordance with some embodiments of the present disclosure.

FIG. 8 is a perspective view of the medical luer connector, in accordance with some embodiments of the present disclosure. FIG. 9 is a bottom perspective view of the protective membrane, in accordance with some embodiments of the present disclosure. Referring to FIG. 8, with continued reference to FIGS. 6 and 7, in some embodiments, the medical luer connector 50 may be a male luer. For example, as illustrated in FIG. 3, the housing or outer surface 55 may have a first luer screw thread 57 formed therein. The medical luer connector 50 may further include a male luer portion 54 defining a lumen 60 extending along a central longitudinal axis $X_1$ of the medical luer connector 50. As depicted in FIG. 7, the central longitudinal axis $X_1$ may be coaxially located with the central longitudinal axis X of the cover 12. In some embodiments, the medical connector 50 may be connected at the proximal end 53 to a syringe (not shown), but in other embodiments, the proximal end 53 of medical connector 50 may be connected to a fluid source (e.g., an IV bag) via an IV tubing or other connection. In some embodiments, the distal end of the medical connector 50 including the male luer portion 54 may be connected to an inlet port of a female luer connector in order to fluidly communicate a lumen of the female luer connector to the lumen of the male luer medical connector 50. Further, in some embodiments, the housing or outer surface 55 may define a mating surface 52 at the distal end 51 for mating and adhering with a corresponding mating portion 24 of the lower surface 16, as described below.

According to various embodiments of the present disclosure, as previously discussed, and similar to the protective membrane 10, the lower surface 16 of the protective membrane 11 may be configured as an interface between the cover 12 and a mating surface of the medical luer connector 50. In particular, lower surface 16 of the protective membrane 11 may include a mating portion 24 which interfaces with and couples to a corresponding mating surface 52 of the male medical luer connector 50. The mating portion 24 may include an adhesive disposed on and/or overlaying the mating portion 24 for adhering to the mating surface 52 of the medical luer connector 50. In some embodiments, the adhesive may be an adhesive coating on the mating portion 24 of the lower surface 16. In some embodiments, the adhesive may be an adhesive layer which is removably coupled to the mating portion 24 of the lower surface 16.

Advantageously, the adhesive may provide a bond between the mating portion 24 and the mating surface 52 having strength and durability that maintains adhesion of the protective membrane 11 to the medical luer connector 50, but also allows for the protective membrane 11 to be removed, detached or otherwise decoupled from the medical luer connector 50 with relative ease using less force as compared to currently existing luer protector caps conventionally used to maintain sterility of medical luer connectors.

Figures 10, 11:
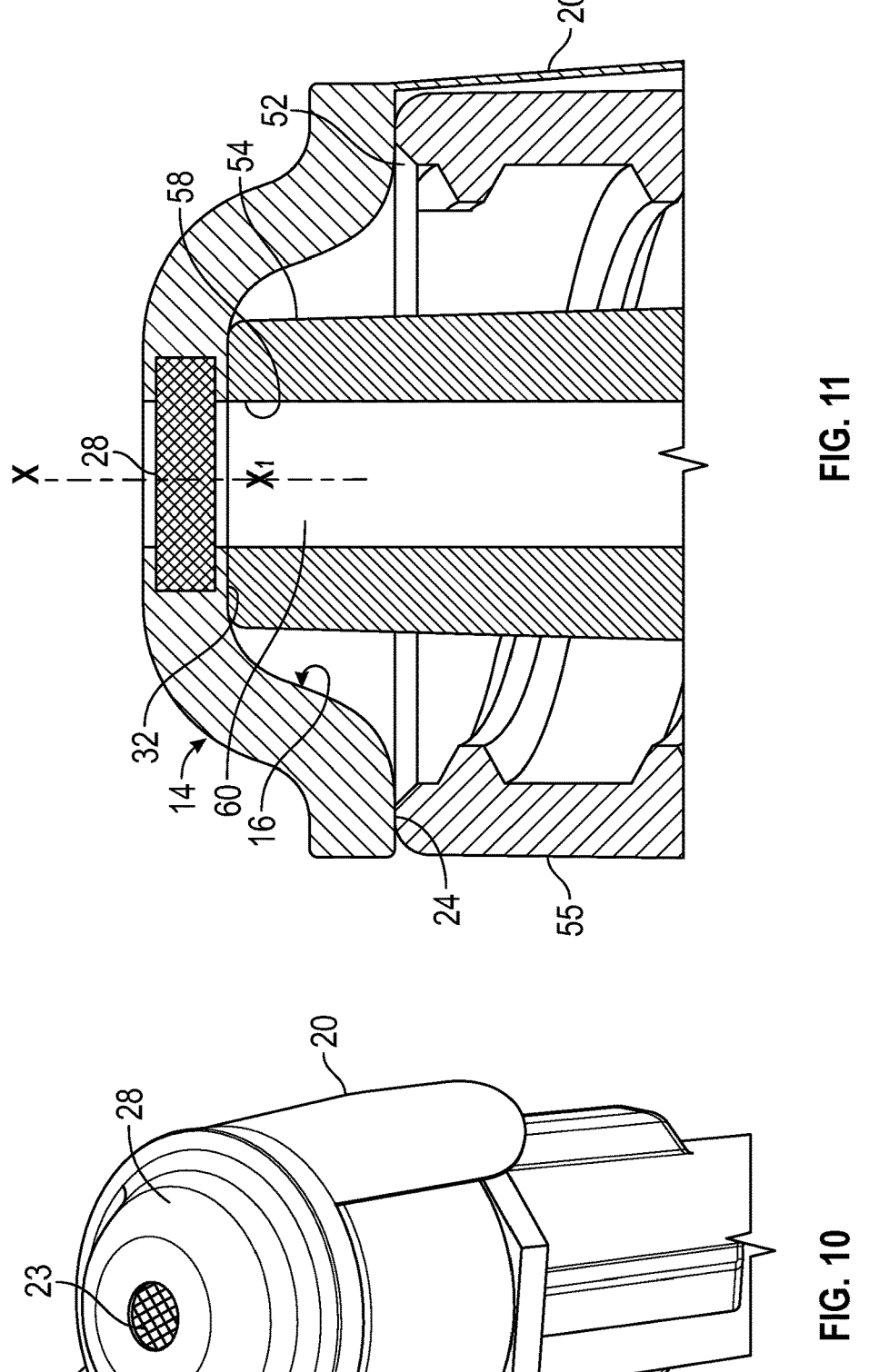
FIG. 10 is a perspective partial view of the medical luer connector including protective membrane in the coupled configuration, in accordance with some embodiments of the present disclosure, in accordance with some embodiments of the present disclosure.
FIG. 11 is a cross-sectional view of the medical luer connector including protective membrane of FIG. 10, in accordance with some embodiments of the present disclosure.

FIG. 10 is a perspective partial view of the medical luer connector 50 including protective membrane 11 in the coupled configuration, in accordance with some embodiments of the present disclosure. FIG. 11 is a cross-sectional view of the medical luer connector 50 including protective membrane 11 of FIG. 10, in accordance with some embodiments of the present disclosure. As depicted, similar to the protective membrane 10, in the coupled configuration of the protective membrane 11 and the medical luer connector 50, the mating portion 24 of the lower surface 16 having the adhesive thereon is adhered to the mating surface 52 of the medical luer connector 50. The adhesion of the lower surface 16 to the mating surface 52 creates a seal therebetween to maintain sterility of internal portions or surfaces, e.g., surfaces 56 and 58 of the medical luer connector 50. As further depicted in FIG. 10, in the coupled configuration of the protective membrane 10 and the medical luer connector 50, the flexible pull tab 20 extends longitudinally along and is removably coupled to an housing or outer surface 55 of the medical luer connector 50. In particular, in some embodiments, the inner surface 25 of the flexible pull tab 20 may interface with and be coupled to the housing or outer surface 55. Due to the flexibility of pull tab 20, the inner surface 25 may be pulled and peeled away or otherwise decoupled from the housing or outer surface 55. The protective membrane 11 may thus be easily removed and discarded from the medical luer connector 50 prior to priming or other use of the IV set. Advantageously, the protective membrane 11 by design as described above is not reusable, thereby avoiding the risk of loss of sterility commonly associated with currently existing protective caps for medial luers which may be reused depending on the clinician or other healthcare professional. For example, once the protective membrane 11 is removed from the medical luer connector, the adhesive may no longer exhibit bond strength to maintain adhesion with and seal the medical luer connector, and thus may not be reusable. In contrast, although reuse of current protective luer caps is not recommended due to loss of cap sterility, it is up to the clinician or other healthcare professional to follow guidelines.

According to various embodiments of the present disclosure, the protective membrane 11 may further include an aperture 21 disposed on the cover 12 and extending through the upper and lower surfaces 14 and 16. In some embodiments, the aperture 21 may be circumferentially disposed about the central longitudinal axis X of the cover 12. As depicted, the aperture 21 may be coaxially disposed with the lumen 60 of the male luer portion 54. As illustrated in FIGS. 10 and 11, a filter 28 may be disposed in the aperture 21 between the upper and lower surfaces 14 and 16 of the cover 12. In some embodiments, the filter 28 may be a hydrophobic filter. The hydrophobic filter 28 may advantageously be disposed about the central longitudinal axis X of the cover 12 over the lumen 60 to permit air to vent out of the lumen 60 to an exterior of the medical luer connector 50 while preventing liquid from exiting to the exterior of the medical luer connector 50. The aforementioned configuration of the protective membrane 11 having the hydrophobic filter 28 is advantageous in that the medical luer connector 50 may be primed without having to remove and discard the protective membrane 10. Accordingly, further sterility of the internal portions of medical connector 50 may be maintained until the IV set having the medical connector 50 is ready for use.

Figure 14:
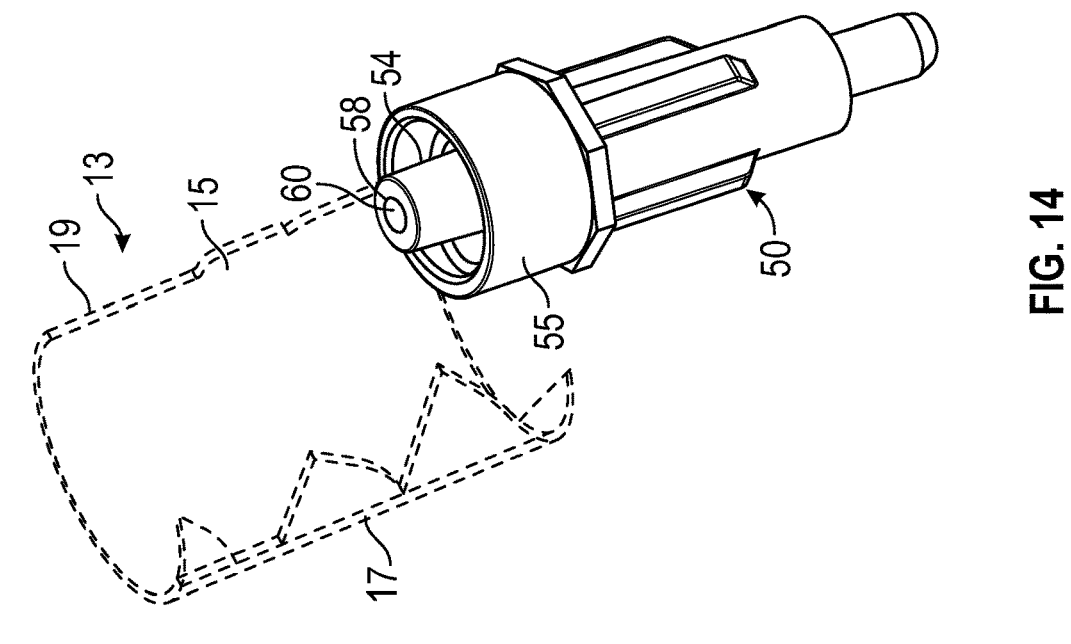
FIG. 14 is a perspective view of the medical luer connector including protective membrane in a decoupled configuration, in accordance with some embodiments of the present disclosure.
Figure 13:
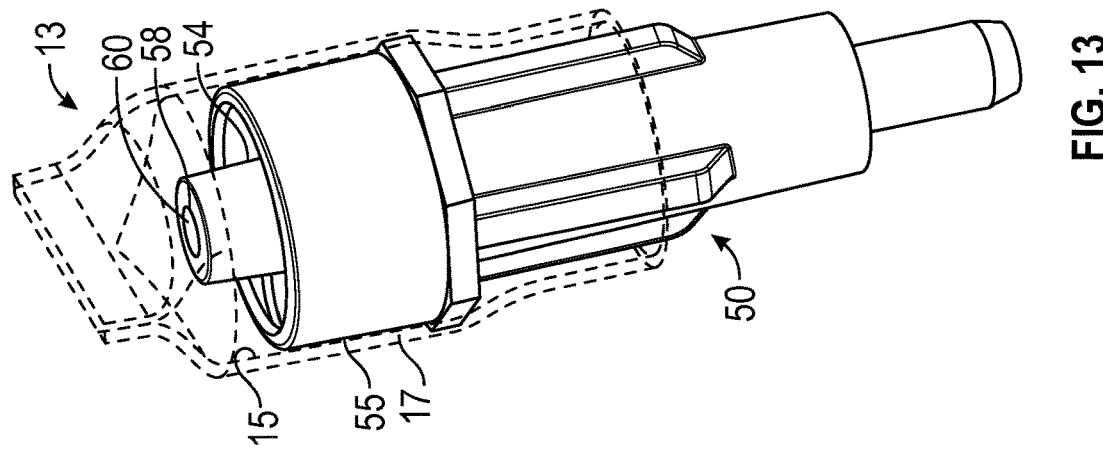
FIG. 13 is a perspective view of the medical luer connector including protective membrane of FIG. 12 in a coupled configuration, in accordance with some embodiments of the present disclosure.
Figure 12:
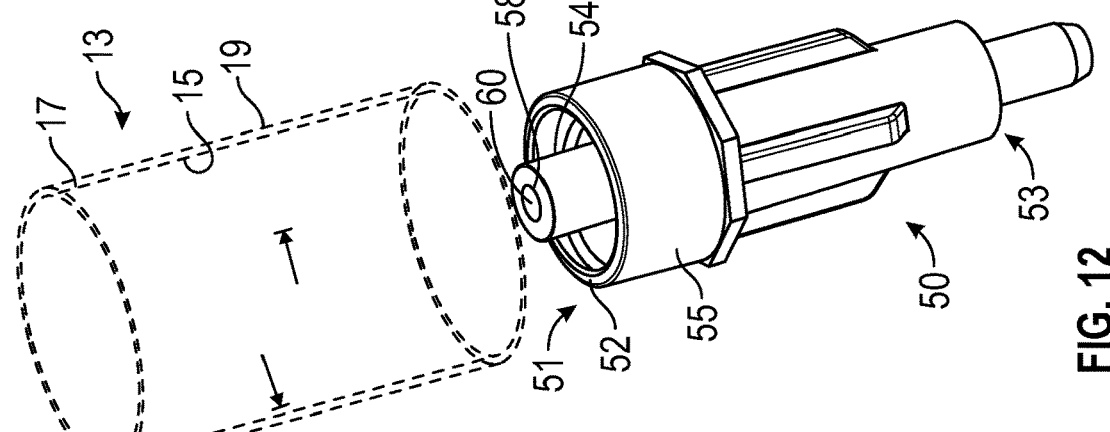
FIG. 12 is a perspective view of the medical luer connector including protective membrane in an un-coupled configuration, in accordance with some embodiments of the present disclosure.

FIG. 12 is a perspective view of the medical luer connector 50 including protective membrane 13 in an uncoupled configuration, in accordance with some embodiments of the present disclosure. FIG. 13 is a perspective view of the medical luer connector 50 including protective membrane 13 of FIG. 12 in a coupled configuration, in accordance with some embodiments of the present disclosure. FIG. 14 is a perspective view of the medical luer connector 50 including protective membrane 13 in a decoupled configuration, in accordance with some embodiments of the present disclosure. According to various aspects of the present disclosure, a protective membrane 13 for a medical luer connector 50 may include a thin-filmed sleeve 17 having an exterior surface 19 and an interior surface 15 for coupling to a housing or outer surface 55 of the medical luer connector 50. The thin-filmed sleeve 17 may be formed of a heat-activatable material which upon exposure to heat is configured to shrink. For example, the thin-filmed sleeve 17 may be formed of a material which when subject to heat may shrink or otherwise reduce in size from a first diameter D1 of the interior surface 15 to a second diameter D2 of the interior surface 15. As illustrated in FIG. 13, when the thin-filmed sleeve 17 is in the shrunken configuration where the second diameter D1 is smaller than the first unshrunken diameter D1, the interior surface 15 may have an interference fit with at least a portion of the housing or outer surface 55 of the medical luer connector 50. In some embodiments, the heat-activatable material of the thin-filmed sleeve may be formed of a polymer plastic material. For example, in some embodiments, the polymer plastic material may be a polyvinyl chloride plastic film.

The aforementioned configuration of the protective membrane formed of a heat-activated material is advantageous in that the shrunken thin-filmed sleeve 17 may tightly seal sterile internal portions of the medical luer connector 50 without adding additional components and weight as a conventional luer protector cap would. Additionally, the configuration of the thin-filmed sleeve 17 is further advantageous in that it allows for the protective membrane 13 to be removed, detached or otherwise decoupled from the medical luer connector 50 with relative ease using less force as compared to currently existing luer protector caps conventionally used to maintain sterility of medical luer connectors.

According to various embodiments of the present disclosure, the protective membrane 13 may further include at least one aperture 22 disposed on the thin-filmed sleeve 17 extending through the exterior and interior surfaces 19 and 15. As illustrated in FIG. 13, the at least one aperture 22 may be isolated, separated, or otherwise spaced apart from the sterile internal portions (e.g., surfaces 56 and 58) of the medical luer connector 50. In some embodiments, a plurality of apertures 22 may be advantageously positioned over the lumen 60 of the male luer portion 54 to permit ethylene oxide sterilization of the medical luer connector 50.

In some embodiments, the protective membrane 13 may be assembled or coupled with the medical luer connector 50 by placing the heat-activated, thin-filmed sleeve 17 having the internal diameter D1 over the medical luer connector, as illustrated in FIG. 12. Heat may then be applied to the thin-filmed sleeve 17, causing the internal diameter of the thin-filmed sleeve to shrink or otherwise decrease to the internal diameter D2 where it fits tightly to the medical luer connector 50 with a tight interference fit, as illustrated in FIG. 13. In some embodiments, the thin-filmed sleeve 17 may be perforated with at least one aperture 22 to allow ethylene oxide sterilization of the medical luer device. In some embodiments, air paths may exist between the thin-filed sleeve 17 and the housing or outer surface 55 due to imperfect sealing between the medical luer connector 50 and the thin-filmed sleeve 17. In operation, the clinician or other healthcare professional may easily remove the protective membrane 13 by tearing the thin-filmed sleeve 17, as illustrated in FIG. 14. The then clinician or other healthcare professional may then prime the IV set when ready to administer an infusion fluid.

The protective membranes of the various embodiments described herein thus offer several advantages as compared with conventional or currently existing protective luer caps which require more bulk material to manufacture, thus adding cost, and which often require more force to be used to remove from the medical luer connectors to which they are attached. For example, the following advantages are realized by the structures of the protective membranes described herein.

The protective membranes of the various embodiments described herein are easier to use than the currently existing protective luer caps. For example, it is not uncommon for current protective luer caps to require a substantial amount of force and be difficult to remove by the clinician. In contrast, the protective membranes for medical luer connectors described herein maintain the sterility of the medical luer connectors with a reduced amount of force required to remove the protective membranes and prepare the medical luer connector for use in an IV set, for example. In particular, as described above, the flexible pull tab of the protective membrane is designed to minimize the amount of force required to peel or otherwise remove the protective membrane from the medical luer connector. The adhesive applied to the protective membrane allows a reduced amount of force as compared to peel or otherwise remove the protective membrane from the medical luer as compared with the amount of force required to remove currently existing protective caps from the medical luer connectors to which they are attached.

Further, the protective membranes of the various embodiments described herein provide enhanced patient safety than the currently existing protective luer caps. For example, although reuse of currently existing protective luer caps is not recommended due to potential loss of cap sterility with multiple uses, it is dependent on the clinician or other healthcare professional to follow guidelines and not reuse the protective cap. The protective membranes of the various embodiments described herein by design are not reusable, thereby avoiding the risk of loss of sterility commonly associated with currently existing protective caps for medial luers which may be reused depending on the clinician or other healthcare professional. For example, once the protective membranes of the various embodiments are removed from the medical luer connector, the adhesive may no longer exhibit bond strength to maintain adhesion with and seal the medical luer connector, and thus may not be reusable. Additionally, since the protective membranes of the various embodiments described herein with the thin-filmed sleeve are removed by being apart away from the medical luer connector, reuse is not possible.

Further, the protective membranes of the various embodiments described herein are cheaper to manufacture than currently existing protective luer caps which require more bulk material to manufacture. Accordingly, the overall cost of an IV set including the protective membranes for medical luer connectors of the various embodiments described herein may be reduced as compared to IV sets incorporating currently existing protective luer caps.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A protective membrane for a medical luer connector, the protective membrane comprising:
   a cover including an upper surface, a lower surface having a mating portion for coupling to a mating surface at a distal end of the medical luer connector, an outer perimetal surface, and at least one aperture positioned at a central longitudinal axis of the cover and extending through the upper surface and the lower surface;
   a flexible pull tab extending from the outer perimetal surface of the cover; and
   an adhesive overlaying the mating portion of the lower surface for adhering to the mating surface at the distal end of the medical luer connector such that the at least one aperture is coaxially located with a longitudinal luer axis of a male luer portion of the medical luer connector and positioned over a lumen of the male luer portion of the medical luer connector to permit ethylene oxide sterilization of the medical luer connector.

2. The protective membrane of claim 1, wherein the flexible pull tab comprises a flap pivotable about the outer perimetal surface for ease of securing and removing the protective membrane from the medical luer connector.

3. The protective membrane of claim 1, wherein in a coupled configuration of the protective membrane and the medical luer connector, the flexible pull tab extends longitudinally along and is removably coupled to an outer surface of the medical luer connector.

4. The protective membrane of claim 1, wherein in a coupled configuration of the protective membrane and the medical luer connector, the mating portion of the lower surface is configured to adhere to the mating surface at a distal end of the medical luer connector to form a seal therebetween to maintain sterility of internal portions the medical luer connector.

5. The protective membrane of claim 1, wherein the adhesive comprises a coating on the mating portion of the lower surface.

6. The protective membrane of claim 1, wherein the adhesive comprises a layer removably coupled to the mating portion of the lower surface.

7. The protective membrane of claim 1, wherein the lower surface of the cover comprises any of a curved or rounded conical profile configured to receive the male luer portion of the medical luer connector therein.

8. The protective membrane of claim 1, wherein the lower surface of the cover comprises a planar profile.

9. A protective membrane for a medical luer connector comprising:
   a medical luer connector comprising a distal end forming a mating surface, a male luer portion forming an inlet port and a lumen extending along a central longitudinal axis of the medical luer connector; and
   a protective membrane comprising a cover, an adhesive, and a flexible pull tab, the cover including an upper surface, a lower surface having a mating portion for coupling to the mating surface of the medical luer connector, an outer perimetal surface, and at least one aperture positioned at a central longitudinal axis of the cover and extending through the upper surface and the lower surface, and the adhesive disposed on the mating portion of the lower surface for adhering to the mating surface at the distal end of the medical luer connector such that the at least one aperture is coaxially located with a longitudinal luer axis of a male luer portion of the medical luer connector and positioned over a lumen of the male luer portion of the medical luer connector; and the flexible pull tab extending from the outer perimetal surface of the cover.

10. The protective membrane of claim 9, wherein the protective membrane comprises a filter disposed in the aperture of the cover, the filter comprises a hydrophobic filter.

11. The protective membrane of claim 10, wherein:
   the hydrophobic filter is disposed about the central longitudinal axis of the cover over the lumen to permit air to vent out of the lumen to an exterior of the medical luer connector while preventing liquid from exiting to the exterior of the medical luer connector.

12. The protective membrane of claim 9, wherein the flexible pull tab is pivotable about the outer perimetal surface for ease of securing and removing the protective membrane from the medical luer connector.

13. The protective membrane of claim 12, wherein in a coupled configuration of the protective membrane and the medical luer connector, the flexible pull tab extends longitudinally along and is removably coupled to an outer surface of medical luer connector.

14. The protective membrane of claim 12, wherein in a coupled configuration of the protective membrane and the medical luer connector, the mating portion of the lower surface is configured to adhere to the mating surface at a distal end of the medical luer connector an creates a seal therebetween to maintain sterility of internal portions of the medical luer connector.

15. The protective membrane of claim 9, wherein the adhesive comprises a coating on the mating portion of the lower surface, or a layer removably coupled to the mating portion of the lower surface.

16. The protective membrane of claim 9, wherein the lower surface of the cover comprises any of a curved or rounded conical profile configured to receive the male luer portion of the medical luer connector in a coupled configuration of the protective membrane and the medical luer connector.

17. A protective membrane for a medical luer connector comprising:

a medical luer connector comprising a distal end forming a mating surface, a male luer portion forming an inlet port, and a lumen extending through the male luer portion and along a central longitudinal axis of the medical luer connector; and a protective membrane comprising a thin-filmed sleeve including an exterior surface, an interior surface for coupling to an outer surface of the distal end of the medical luer connector, and a plurality of apertures extending through the exterior surface and the interior surface of the thin-filmed sleeve;

wherein the thin-filmed sleeve comprises a heat-activatable material, which upon exposure to heat is configured to shrink from a first diameter of the interior surface to a second diameter of the interior surface where the interior surface has an interference fit with at least a portion of the outer surface of the medical luer connector and seals a sterile portion of the medical luer connector, and the plurality of apertures are configured to be positioned over the lumen of the medical luer connector to permit ethylene oxide sterilization of the medical luer connector.

18. The protective membrane of claim 17, wherein the heat-activatable material of the thin-filmed sleeve comprises a polymer plastic material.

19. The protective membrane of claim 18, wherein polymer plastic material comprises a polyvinyl chloride plastic film.

20. The protective membrane of claim 17, wherein the plurality of apertures are circumferentially disposed about a central longitudinal axis of the sleeve.

* * * * *